United States Patent [19]
See

[11] Patent Number: 6,046,240
[45] Date of Patent: Apr. 4, 2000

[54] METHODS FOR TREATING FEMALE SEXUAL DYSFUNCTION

[75] Inventor: Jackie R. See, Fullerton, Calif.

[73] Assignee: Harvard Scientific Corporation, Reno, Nev.

[21] Appl. No.: 09/301,023

[22] Filed: Apr. 28, 1999

Related U.S. Application Data

[60] Provisional application No. 60/099,431, Sep. 8, 1998, and provisional application No. 60/083,965, May 1, 1998.

[51] Int. Cl.[7] .................................................... A61K 31/19

[52] U.S. Cl. ............................................................ 514/573

[58] Field of Search ............................................... 514/573

[56] References Cited

U.S. PATENT DOCUMENTS

| | | | |
|---|---|---|---|
| 5,718,917 | 2/1998 | See | 424/450 |
| 5,877,216 | 3/1999 | Place et al. | 514/573 |
| 5,891,915 | 4/1999 | Wysor et al. | 514/573 |

*Primary Examiner*—Raymond Henley, III
*Attorney, Agent, or Firm*—Christie, Parker & Hale, LLP

[57] ABSTRACT

A method for treating female sexual dysfunction or for female sexual enhancement comprises administering to the vagina a composition comprising a prostanoid compound having a vasodilating effect in a pharmaceutically acceptable vehicle. The amount of prostanoid compound administered ranges from about 0.05 mg to about 3 mg, and preferably from about 0.125 mg to about 1 mg. Preferably the prostanoid compound is prostaglandin E-1 and the pharmaceutically acceptable vehicle is methylcellulose.

21 Claims, 3 Drawing Sheets

METHODS FOR TREATING FEMALE SEXUAL DYSFUNCTION

CROSS-REFERENCE TO RELATED APPLICATIONS

This application is based on U.S. Provisional Application Ser. No. 60/099,431, filed Sep. 8, 1998, and U.S. Provisional Application Ser. No. 60/083,965, filed May 1, 1998.

FIELD OF THE INVENTION

This invention relates to the methods for treating female sexual dysfunction and for female sexual enhancement, and more particularly to the administration of a prostanoid compound to a female intravaginally or extravaginally.

BACKGROUND OF THE INVENTION

Recent studies have revealed that approximately 10 million women in the United States between the ages of 50 and 74 reported a lack of lubrication on 229 million sexual intercourse occasions. In fact, it was found that over fifty-eight percent of 260 females surveyed were affected by sexual dysfunction, as defined as pain or discomfort during sexual intercourse, diminished vaginal lubrication, delayed vaginal engorgement, increased time for arousal, diminished ability to reach orgasm, or diminished clitoral sensation.

An animal model of this syndrome was developed by Goldstein and Berman (Int. J. Impot. Res. 10 Suppl. 2:S84–90; S98–101, 1998, the disclosure of which is incorporated herein by reference). These investigators undertook diagnostic studies assessing the hemodynamic integrity of the ilio-hypogastric-pudendal arterial bed to the vagina and clitoris and new oral/topical pharmacologic strategies for enhancing vaginal/clitoral blood flow in patients with vasculogenic female sexual dysfunction. They observed that there was a growing body of evidence that women with sexual dysfunction would commonly have physiologic abnormalities, such as vasculogenic female sexual dysfunction, contributing to their overall sexual health problems.

Park et al. (Int. J. Impot. Res. 9:27–37, 1997, the disclosure of which is incorporated herein by reference) have shown that female sexual dysfunction may be related in part to vasulogenic impairment of the hypogastric-vaginal/clitoral arterial bed. In order to investigate this theory under a controlled experimental situation, they developed an animal model of vaginal engorgement insufficiency and clitoral erectile insufficiency. They achieved pelvic nerve stimulated vaginal engorgement and clitoral erection in control normal diet New Zealand White female rabbits and atherosclerotic balloon injury of aorto-iliac arteries and 0.5% cholesterol diet New Zealand White female rabbits. After 16 weeks, novel hemodynamic variables, including vaginal wall and clitoral blood flow, vaginal wall and clitoral intracavemosal pressure, vaginal length, vaginal luminal pressure, blood levels of cholesterol and triglycerides, aorto-iliac angiography and vaginal wall and clitoral erectile tissue histology, were recorded in the two groups of rabbits. Their results indicate that pelvic nerve stimulation induced vaginal hemodynamic changes, and there was significantly less increase in blood flow, wall pressure and length changes in atherosclerotic rabbits compared to the control rabbits. Histologic examination of clitoral erectile tissue demonstrated cavernosal artery atherosclerotic changes and diffuse vaginal and clitoral fibrosis. Aorto-iliac angiography in atherosclerotic animals revealed diffuse moderate to severe atherosclerotic occlusion. They conclude that vaginal engorgement and clitoral erection depend increased blood inflow.

Present day management of women with sexual arousal disorder, especially those with diminished vaginal lubrication and painful penetration is based on psychologic, hormonal and "artificial lubricant" interventions. The pathophysiology of vaginal engorgement insufficient may be, in part, related to vascular impairment.

Prostanoid compounds, such as prostaglandin E-1 (PGE-1), have been used as an adjunct to improving blood flow in arterial angioplasty procedures. See See et al., Advances in Prostaglandin, Thromboxane and Leukotriene Res., 17:266–70, 1987; See et al., Applied Cardiopulmonary Pathophysiology 2:193–98, 1998, the disclosures of which are incorporated herein by reference. Prostanoid compounds have also been used in the treatment of male erectile dysfunction. For example, U.S. Pat. No. 5,718,917, the disclosure of which is incorporated herein by reference, discloses a method for treating erectile dysfunction comprising administering prostaglandin-containing liposomes to the penis.

SUMMARY OF THE INVENTION

The present invention provides methods for treating female sexual dysfunction and for female sexual enhancement. The invention is also directed to methods for enhancing blood flow in the vagina of a patient. The methods comprise administering a composition comprising a prostanoid compound having a vasodilating effect in a pharmaceutically acceptable vehicle to the vagina.

A preferred dose of the composition contain less than 3 mg of the prostanoid compound, more preferably from 0.05 mg to about 3 mg, more preferably 0.05 mg to about 2 mg, and still more preferably about 0.125 mg to about 1 mg of the prostanoid compound. In a preferred embodiment, the prostanoid compound is contained within liposomes, which preferably are lyophilized to enhance the stability of the compositions. In a preferred embodiment, the prostanoid composition is lyophilized. Preferably the prostaglandin is prostaglandin E-1 ("PGE-1").

DESCRIPTION OF THE DRAWINGS

These and other features and advantages of the present invention will be better understood by reference to the following detailed description when considered in conjunction with the accompanying drawings wherein.

DETAILED DESCRIPTION

Figure 1:
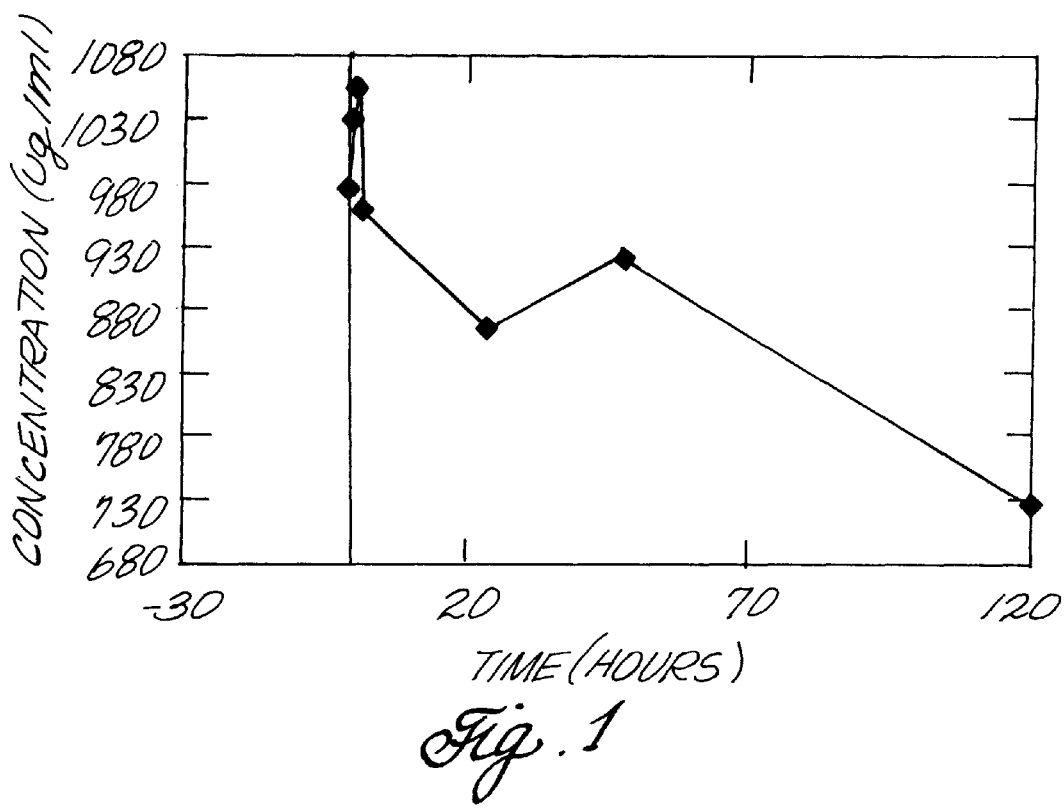
FIGS. 1 to 4 are tables showing the graphic distribution of PGE-1 concentration over the duration of a stability study.
Figure 2:
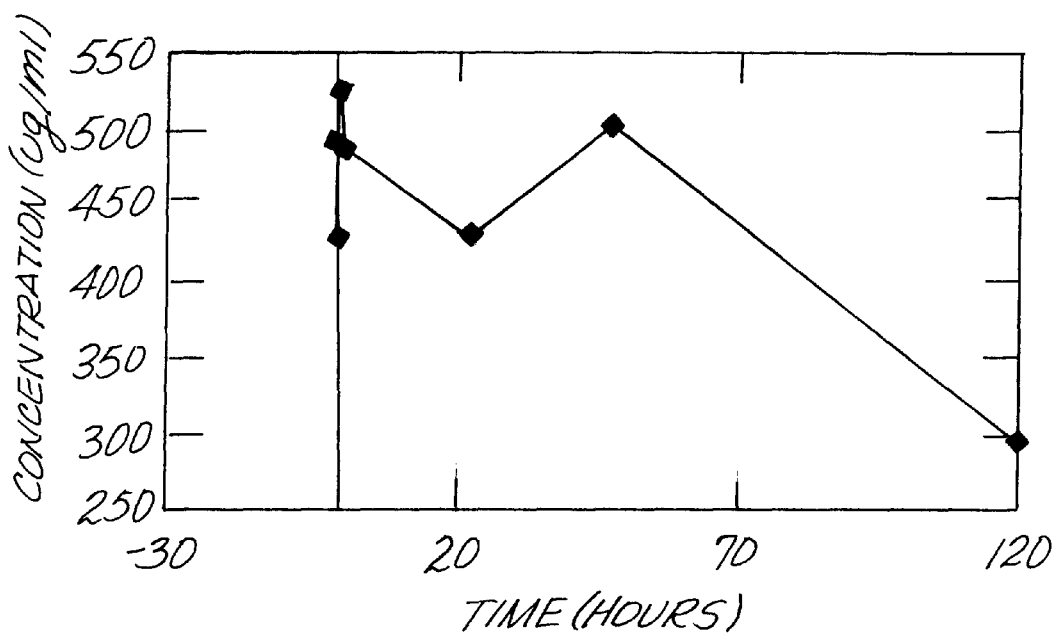
Figure 3:
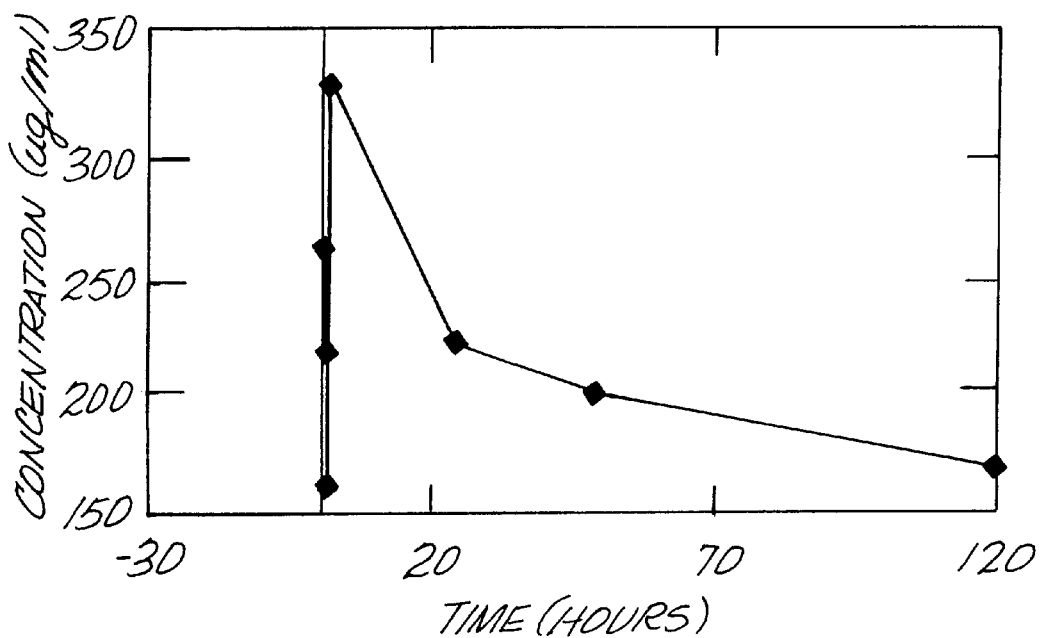
Figure 4:
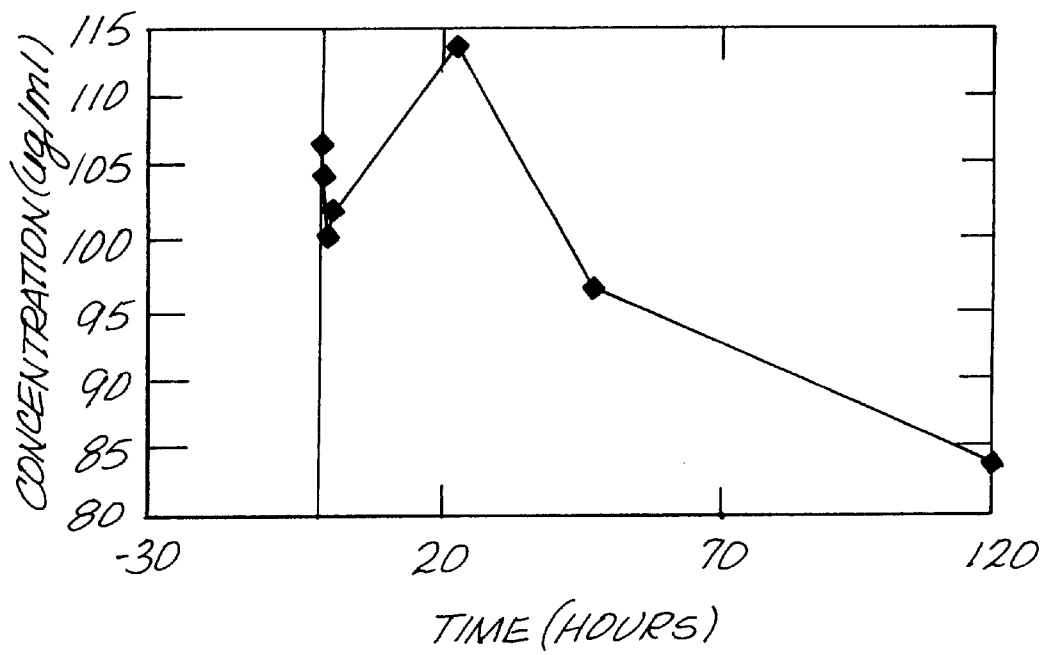

The present invention is directed to methods for treating female sexual dysfunction and for female sexual enhancement. As used herein, female sexual dysfunction includes pain or discomfort during sexual intercourse, diminished vaginal lubrication, delayed vaginal engorgement, increased time for arousal, diminished ability to reach orgasm, and diminished clitoral sensation. The invention is also directed to methods for enhancing blood flow in the vagina of a patient. The methods comprise administering a composition comprising a prostanoid compound having a vasodilating effect in a pharmaceutically acceptable vehicle to the vagina, externally and/or internally.

As used herein, the term "vagina" refers not only to the genital canal that extends from the uterus to the vulva, but also to the external genitalia, including the clitoris, labium anterium, labium posterius, labia majora, and labia minora. More specifically, the clitoris contains erectile tissue, blood supply and innervation in the female similar to that in the penis of the male. It has been discovered that the application of the composition to the clitoris increases the blood supply to engorge the clitoris by the same mechanism as engorgement of vascular tissue of the penis in the male. The composition's effects on the innervation of the erectile tissue and sensory tissue of the clitoris in the female is similar to its effects on the comparable male tissue.

Prostanoid compounds suitable for use in the present invention include prostaglandin E (PGE), including PGE-1, PGE-2 and PGE-3, prostaglandin A (PGA), including PGA-1, prostaglandin F (PGF), including PGF-2, prostaglandin D (PGD), including PGD-2, prostacylins, thromboxanes, leukotrienes, 6-keto-PGE-1 derivatives, carbacyclin derivatives, PGD-2 derivatives and the like, and synthetic analogs of any prostanoid compounds. PGE-1 and PGE-2 are preferred, and PGE-1 is the most preferred. Other examples of suitable prostanoid compounds are described in U.S. Pat. No. 4,955,878, the disclosure of which is incorporated herein by reference. The prostanoid compound is preferably provided in crystal, liquid or lyophilized form within the vehicle.

A preferred dose contain less than 3 mg of the prostanoid compound, more preferably from 0.05 mg to about 3 mg, more preferably 0.05 mg to about 2 mg, and still more preferably about 0.125 mg to about 1 mg of the prostanoid compound. The dose of prostanoid compound should be maintained at these relatively low levels due to the potential toxicity of the prostanoid compound caused by rapid absorption of the prostanoid compound across the vaginal tissue.

The pharmaceutically acceptable vehicle is a composition to facilitate the application of the prostanoid compound. Suitable vehicles include, for example, lotions, gels and liquids. A particularly preferred vehicle is methylcellulose, such as that sold under the name KY JELLY. Preferably the vehicle has a near-neutral pH. Other examples of vehicles include water, silicone, waxes, polyethylene glycol, propylene glycol and sugars. The compositions are formed by uniformly mixing the prostanoid compound in the vehicle according to methods know to those skilled in the art.

In a preferred embodiment, the prostanoid compound is contained within liposomes. The liposomes of the present invention may be made of any suitable phospholipid, glycolipid, derived lipid, and the like. Examples of suitable phospholipids include phosphatide choline, phosphatidyl serine, phosphatidic acid, phosphatidyl glycerin, phosphatidyl ethanolamine, phosphatidyl inositol, sphingomyelin, dicetyl phosphate, lysophosphatidyl choline and mixtures thereof, such as soybean phospholipids, and egg yolk phospholipids. Suitable glycolipids include cerebroside, sulphur-containing lipids, ganglioside and the like. Suitable derived lipids include cholic acid, deoxycholic acid, and the like. The presently preferred lipid for forming the liposomes is egg phosphatidylcholine.

The liposomes may be formed by any of the known methods for forming liposomes and may be loaded with prostaglandin according to known procedures. Known methods for forming liposomal prostaglandin (PG) are described, for example, in PCT Application No. PCT/US88/01714 and European Patent Application No. EP 0,512,916A2, both assigned to the Liposome Company, and European Patent Application No. EP 0,416,527A2 assigned to the Green Cross Corporation, and the references disclosed in those applications, all of which are incorporated herein by reference. What is formed is an emulsion comprising liposomal PG.

It is preferred that the liposomes used in the present invention have an average mean diameter from about 20 nm to about 1000 nm and preferably of from about 100 nm to about 200 nm. An average mean diameter of about 140 nm is particularly preferred. Liposomes larger than about 1000 nm are not preferred because they are difficult to make. Liposomes smaller than about 20 nm are usable but not preferred because they are difficult to make.

Accordingly, the liposomes produced are preferably treated to reduce their size and to produce a homogeneous population. This may be accomplished by conventional techniques such as extrusion through a filter preferably of 100 to 500 nm pore size, the filter being either the straight path or tortuous path type. Other methods of size reducing the liposomes to a homogenous size distribution are ultrasonic exposure, the French press technique, hydrodynamic shearing, homogenization using, for example, a colloid mill or Gaulin homogenizer or microfluidization techniques. Microfluidization is presently preferred, and is described in U.S. Pat. No. 4,533,254 to Cook, et al., the disclosure of which is incorporated herein by reference. In a preferred microfluidization procedure, the liposomal emulsion is forced at high pressure through a small diameter opening, splattered onto a wall and then collected.

In a particularly preferred embodiment of the invention, the liposomes are passed one to ten, and preferably four, times through an M-110 Series Laboratory Microfluidizer manufactured by Microfluidics Corporation at a pressure of, e.g., 14000–16000 pounds per square inch to achieve a generally homogenous population of liposomes having an average mean diameter of about 140 nm.

Lyophilization of the prostanoid compound or liposomal prostanoid compound may be accomplished by any method known in the art. Such procedures are disclosed, for example, in U.S. Pat. No. 4,880,836 to Janoff, et al., the disclosure of which is incorporated herein by reference. In the case of liposomes, lyophilization procedures preferably include the addition of a drying protectant to the liposome suspension. The drying protectant stabilizes the liposomes so that the size and content are maintained during the drying procedure and through rehydration. Preferred drying agents are saccharide sugars including dextrose, sucrose, maltose, manose, galactose, raffinose, trehalose lactose, and triose sugars which are preferably added in amounts of about 5% to about 20% and preferably about 10% by weight of the aqueous phase of the liposomal suspension. Dextrose, sucrose and maltose are presently preferred. Manitol may be used in conjunction with any of the saccharides. Additional preservatives such as BHT or EDTA, urea, albumin, dextran or polyvinyl alcohol may also be used.

In the case of liposomal PG, to determine the amount of liposomal PG necessary to deliver the desired dose of prostaglandin, it was necessary to determine how much prostaglandin is present. Analysis using a standard prostaglandin E-2 ELISA test established that prostaglandin can be loaded into liposomes in amounts as high as 20% to 40% by weight. However, it is preferred that the prostaglandin be present in the liposomes in an amount of from about 2% to about 3% by weight. A particularly preferred lyophilized liposomal PG composition comprises 44 mg egg phosphotidylcholine, 75 mg maltose and 1 mg prostaglandin E-1.

If desired, the composition can further comprise a surfactant to enhance the bioavailability of the prostanoid compound. The surfactant reduces the interfacial tension between the pharmaceutically acceptable vehicle and the prostanoid compound, and also reduces the interfacial tension between the prostanoid compound and the vaginal mucosa. When the prostanoid compound is encapsulated in liposomes, a surfactant can also enhance the dissolution of the liposomes. Suitable surfactant formulations for use in the present invention are described in U.S. Pat. No. 5,207,220, the disclosure of which is incorporated herein by reference. Preferably the surfactant is present in the composition in an amount ranging from about 0.02% to about 2% by weight.

Other agents can be included in the composition of the invention, including, but not limited to, other vasodilators, alpha-adrenergic inhibitors, prazocin, papaverine, phentolamine, vasointenstinal peptide (VIP), estrogen and estrogen-like compounds, alpha-adrenergic receptor mediators, nitroglyerin compounds and the like.

EXAMPLE 1

Preparation of Lyophilized PGE-1 Liposomes

Liposomal PGE-1 in accordance with the present invention was prepared according to the following procedure.

1. 2250 ml of water (double distilled) to beaker (keep cool) and set with a nitrogen sparge for at least 30 minutes.
2. Add 225 gms of maltose (Sigma M5885) to the water and mix until dissolved. Keep the nitrogen sparge going. Mixture at pH of 4.81.
3. In another beaker 10.59 gms of egg phosphatidylcholine (EPC) (Sigma) is combined with 8.38 ml of ethanol (anhydrous, Sigma E3884) and mixed until dissolved. To this add 67.5 mg of BHT and mix until dissolved. To this mixture add 2160 mg of PGE-1 and mix until dissolved. Use the remaining 4.19 ml of ethanol to rinse any remaining PGE-1 in the weighing container into the mixture.
4. Draw the ethanol solution into a 10 ml glass syringe and add to the maltose solution over 11 minutes with continued nitrogen sparge. Keep ph <7.0 (goes into microfluidizer at ph 4.81). Measure. Hand blade mixture. Keep everything cool 1.5 degrees C.
5. Microfluidizer. Four (4) passes through the microfluidizer 110° F.: 9,000 Units

|  | Total Weight of Materials to be Used* | Based on Previous Run (886 Units)* |
| --- | --- | --- |
| EPC | 10.59 grams | 107.573 grams |
| Maltose | 225 grams | 2,285.55 grams |
| Ethanol | 12.57 ml | 127.69 ml |
| BHT | 67.5 mg | 685.66 mg |
| PGE-1 | 2160 mg | 21,941 grams |
| (USP)Water | 2250 ml | 22,855.5 ml |

Pressure 16,000 PSI
Caution-keep acidic, keep temp (melting point 115 degrees)
Note-Maltose melting point 102–103 degrees Centigrade
*Multiplier +10.158

6. Take 2.7 ml of the finished product and lyophilize in approximately 1,000 6 ml Wheaton eye dropper bottles.

Lyophilization was accomplished according to the following cycle:

1. Shelf at ≦−45° C. for at least one (1) hour before loading.
2. Load product and keep at ≦−45° C. for twelve (12) hours.
3. Vacuum to ~50 μ.
4. Shelf temperature maintained at −28° C. to −20° C. for 59 hours.
5. Shelf temperature rose from −20° C. to −5° C. during subsequent ten (10) hours.

Visually product needed extra time at −20° C.

6. Shelf reset at −22° C. and maintained at −22° C. to −18° C. for thirty-six (36) hours.
7. Shelf reset +25° C. and held at 25° C. for 48 hours.

It is anticipated that the following lyophilization cycle will provide the same results in a shorter time.

1. Shelf to ≦−45° C. for at least one (1) hour before loading.
2. Load product, keep at ≦−45° C. for at least six (6) hours.
3. Vacuum to ≦100 μ.
4. Shelf to −28° C. for 50 hours.
5. Shelf to +25° C. for 40–50 hours.

EXAMPLE 2

Vaginal Application of PGE-1 in KY Jelly on Rabbits

Treatment lotion was prepared as follows. Liposomal PGE-1, made in a manner similar to that described above, was prepared. Six sets of treatment lotion having different concentrations of PGE-1 were prepared by combining 1 gm of KY Jelly (methylcellulose, available from Ortho Pharmaceutical Corporation) with liposomal PGE-1 to achieve a final amount of PGE-1 equal to 1.5, 1.0, 0.5, 0.25, and 0.125 mg, and without liposomal PGE-1 as a control. The treatment lotion was kept refrigerated until used.

Thirty ten-week old female rabbits were kept in cages and fed, watered and observed daily. The treatment lotion was applied daily to the rabbits over a period of fourteen days, and the rabbits were observed daily. The rabbits were sacrificed 1+ hours after the final dose was applied.

Each rabbit was given 100 mg of Xylazine and 100 mg of ketamine intramuscularly using a 3 cc syringe and a 22 gauge needle. Once the rabbit was under anesthesia, the chest and groin area was clipped, and the animal was brought into the surgical area. Blood was drawn by heart puncture and transferred to a 7 cc heparin tube. The chest was then opened, and the heart was removed to insure a quick and painless death. Three sections were taken from the vaginal area and placed in 2 cc of formalin. After the surgeries were complete, the blood was centrifuged for 10 minutes, and the plasma was frozen. The vaginal sections were fixed for at least 24 hours and were then stained and fixed to slides.

In the rabbits treated with the PGE-1 containing compositions, increased vascular engorgement, vasodilation and hyperemia were observed compared to the rabbits treated with controls. Moreover, no systemic effects were observed, as indicated by a lack of degradation products.

EXAMPLE 3

Reconstitution Study for Topical Liposomal PGE-1

A 1.0 mg aliquot of lyophilized liposomal PGE-1 was mixed with 1.0, 2.0, 4.0 and 8.0 g aliquots of KY Jelly to determine the stability of PGE-1 in the presence of KY Jelly. Each preparation was mixed thoroughly by vortexing. The resulting mixtures contained 1.0 mg/ml, 0.5 mg/ml, 0.25 mg/ml and 0.125 mg/ml PGE-1, respectively. A 0.5 g aliquot of each preparation was transferred to an Eppendorf centrifuge tube along with a 0.5 ml aliquot of acetonitrile. Each preparation was extracted by vortexing thoroughly. After extraction, each preparation was centrifuged, and the liquid supernatant was transferred to an autosampler vial for analysis.

In addition, 1.0 mg/ml and 0.5 mg/ml preparations were extracted using 2 ml and 4 ml aliquots of acetonitrile for comparison. The different preparation procedures were utilized to determine the best extraction process that would product the most homogeneous mixture for the accurate identification and quantitation of the active ingredient, PGE-1.

All test preparations were extracted and analyzed by HPLC at 15, 30, 60 and 120 minute intervals and at 1, 2 and 5 days. The results were evaluated for the accurate identification and quantitation of PGE-1 and for any trends in loss of concentration over time.

Tables 1 to 4, below, show the individual assay results obtained for each preparation, and FIGS. 1 to 4 provide a graphic distribution of PGE-1 concentration over the duration of the study. The results indicate that the 1.0 mg/ml lyophilized liposomal PGE-1 topical product is stable in KY Jelly for at least 2 days and does not degrade to metabolites.

TABLE 1

Stability of PGE in K.Y. Jelly (1000 ug/ml PGE)

| Time | Prep1 | Prep2 | Prep3 | Average (ug/ml) |
|---|---|---|---|---|
| 15 min | 946 | 969.8 | 1011.5 | 975.8 |
| 30 min | 997.8 | 1027 | 1073.7 | 1032.8 |
| 60 min | 1109.8 | 942.8 | 1116.9 | 1056.5 |
| 120 min | 987.1 | 941.7 | 945.4 | 958.1 |
| 1 day | 882.5 | 843.5 | 861.9 | 862.6 |
| 2 days | 942.6 | 920.1 | 898.6 | 920.4 |
| 5 days | 738.8 | 751.2 | 685.1 | 725.1 |

TABLE 2

Stability of PGE in K.Y. Jelly (500 ug/ml PGE)

| Time | Prep1 | Prep2 | Prep3 | Average (ug/ml) |
|---|---|---|---|---|
| 15 min | 471.3 | 297 | 518.3 | 428.9 |
| 30 min | 549.6 | 434 | 486.6 | 490.1 |
| 60 min | 450 | 536.9 | 581.5 | 522.8 |
| 120 min | 504.4 | 484.5 | 463 | 484 |
| 1 day | 458.1 | 441.6 | 390.7 | 430.1 |
| 2 days | 497.9 | 507.4 | 501.3 | 502.2 |
| 5 days | 281.8 | 303.6 | 294.9 | 293.4 |

TABLE 3

Stability of PGE in K.Y. Jelly (250 ug/ml PGE)

| Time | Prep1 | Prep2 | Prep3 | Average (ug/ml) |
|---|---|---|---|---|
| 15 min | 222.4 | 221.5 | 203.2 | 215.7 |
| 30 min | 247.2 | 233 | 301.7 | 260.6 |
| 60 min | 149.3 | 190.4 | 143.4 | 161 |
| 120 min | 222.6 | 378.2 | 380.8 | 327.2 |
| 1 day | 213.9 | 218.5 | 226 | 219.5 |
| 2 days | 179.3 | 227.9 | 188.8 | 198.7 |
| 5 days | 186.3 | 144.9 | 171.2 | 167.5 |

TABLE 4

Stability of PGE in K.Y. Jelly (125 ug/ml PGE)

| Time | Prep1 | Prep2 | Prep3 | Average (ug/ml) |
|---|---|---|---|---|
| 15 min | 101.3 | 114.6 | 103.5 | 106.5 |
| 30 min | 105.2 | 108.8 | 99.1 | 104.4 |
| 60 min | 106.3 | 102.3 | 91.9 | 100.2 |
| 120 min | 108.3 | 101.4 | 96 | 101.9 |
| 1 day | 111.3 | 111.6 | 118.3 | 113.7 |
| 2 days | 97.8 | 103.1 | 88.4 | 96.4 |
| 5 days | 87.4 | 84.9 | 79.1 | 83.8 |

EXAMPLE 4

PGE-1 was encapsulated in multilamellar liposomes in a manner similar to that described in Example 1, above. Three different preparations were made: a control (1 gram of KY Jelly without any liposomal PGE-1), a low dose preparation (0.25 mg of liposomal PGE-1 uniformly mixed with 1 gm of KY Jelly), and a high dose preparation (2.0 mg of liposomal PGE-1 uniformly mixed with 1 gm of KY Jelly).

Female New Zealand rabbits were used as the animal model. MRI studies were initiated when the rabbits were 5 weeks old as the baseline study where the control preparation (C) was applied to the vagina. At that time, the average weight of the rabbits was 1510±486 gm. A second study was performed a week later when the rabbits were 6 weeks old using the low dose preparation (LD). The average weight of the rabbits during the second study was 1746±1444 gm. A third study was performed 2 weeks after the baseline study when the animals were 7 weeks old where the high dose preparation (HD) was applied. The average weight of the animals during the final study was 2011±297 gm. In each study, a sufficient amount of the cream to cover the whole vaginal area, approximately 1 gm (approximately 2 to 3 ml), was used. Ten rabbits were studied longitudinally for 3 weeks using control, low and high doses as defined above.

Dynamic MRI experiments were carried out on all of the rabbits when they were 5, 6 and 7 weeks old. All experiments were performed on a GE 1.5T Signa Scanner using the GE linear extremity head coil. After the rabbit was anesthetized using a 25 mg/kg dose of Ketamine, a 25 gauge butterfly needle was placed into the ear vein for the injection of the contrast agent, and then the rabbit was placed into the coil in a prone position. A fast spin echo (FSE) pulse sequence (TR=3s, TE=112ms, 8 echo train) was applied to acquire the T2-weighted images as localizer and anatomic images. A spin echo (SE) pulse sequence was applied to acquire the dynamic T1-weighted images before and after injection of Gd-DTPA (gadolinium diethylenetriamine pentaacetic acid) (0.1 mmol/kg, Magnevis, Berlex Lab. Inc.) as a short bolus. The dynamic study started 15 min after the liposomal PGE-1 preparation was applied.

The alternations in blood flow in response to the use of liposomal PGE-1 were monitored using dynamic contrast enhanced MRI and compartmental modeling as generally described by Su and Nalcioglu (Magn. Reson. Med. 32(6):714–24, 1994; Magn. Res. Med. 34:402–11, 1995; Magn. Res. Med. 39:259–69, 1998; Magn. Res. Med. 36:868–77, 1996, the disclosures of which are incorporated herein by reference). This technique yields spatially resolved information regarding vascular volume and tissue permeability. The physiologic parameters are obtained by generating signal intensity time course curves for each pixel and subtracting the pre-contrast baseline values from each point, resulting in a signal enhancement curve for each pixel. The compartmental model is then used to derive vascular volume and tissue permeability by using a nonlinear least squares fit through the signal enhancement vs. time curve. The details of the method are described in the above references by Su and Nalcioglu.

In the present study the signal enhancement at 3 minutes post contrast agent injection was used as a measure of blood flow through the tissue under consideration. Two regions of interest (ROI) covering the vagina (VG) and leg muscle (MS) as a reference were used in the analysis. In order to eliminate any systemic response we divided the signal enhancement in vagina by that of the leg muscle (VG/MS). This provided us with a relative enhancement, or blood flow, of the vagina compared to muscle. This value was calculated for each rabbit and for all 3 doses. The relative blood flow enhancement, VG/MS, was then averaged over 10 rabbits for each dose.

Figure 5:
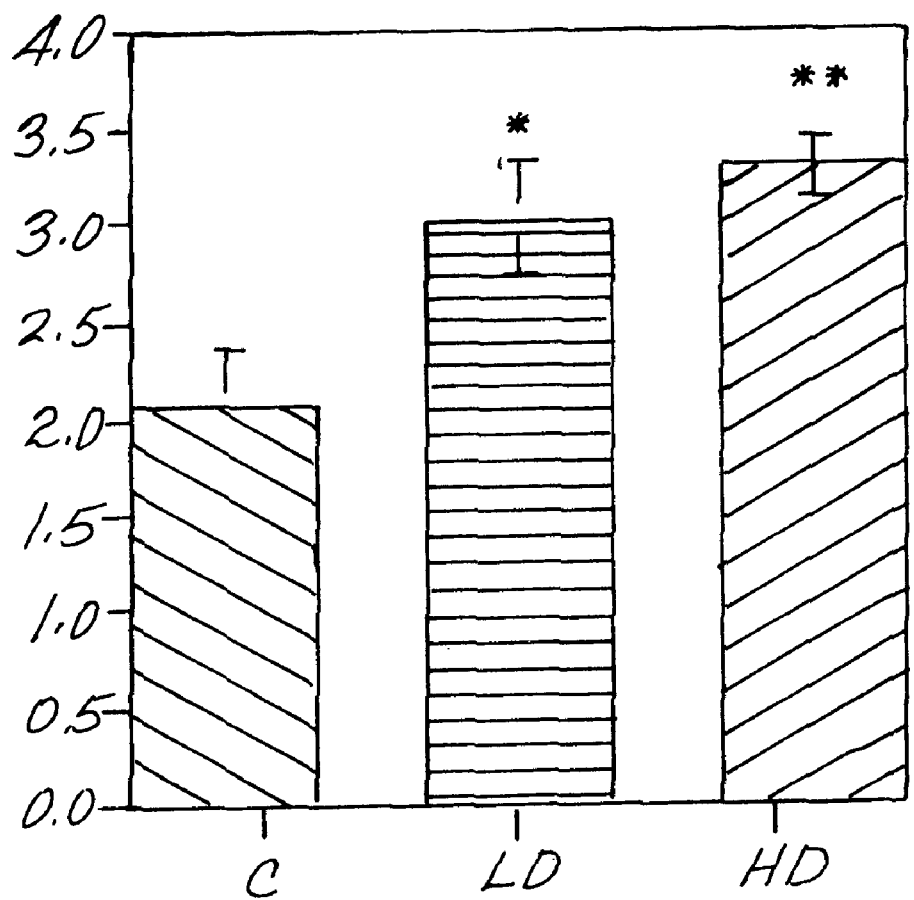
FIG. 5 is a table showing the relative blood flow in the vaginal muscle compared to the leg muscle upon administration of a PGE-1 composition to the vagina.

MR images were analyzed, and they demonstrated that the blood flow was higher with the low dose preparation then with the control, which did not contain any PGE-1. The results are shown in FIG. 5. Vaginal blood flow with the low dose preparation was higher than the control with a statistical significance of p<0.01, and vaginal blood from with the high dose preparation was higher than the control with a statistical significance of p<0.005. Application of liposomal PGE-1 into the vagina caused a 45.9% increase in vaginal blood flow with a preparation containing 0.25 mg liposomal PGE-1, and a 59.5% increase with a preparation containing 2.0 mg liposomal PGE-1. The blood flow difference between the low dose preparation and low dose preparation was not statistically significant. Additionally, it was observed that the blood flow in the leg did not change significantly when the preparation containing PGE-1 was applied to the vagina. Table 5 shows the average blood flow in the leg muscle at each time point for the entire group of 10 rabbits. Table 6 shows the average relative blood flow in the vagina with respect to the leg muscle under the same conditions. The first row gives the relative average vaginal blood flow with respect to muscular blood flow at baseline with KY Jelly alone, at week 1 with a low dose preparation, and finally at week 2 with a high dose preparation. The second row gives the standard error in each measurement.

TABLE 5

Blood flow in the Leg Muscle

|  | Control | Low Dose | High Dose |
| --- | --- | --- | --- |
| MS - mean | 32.15 | 28.87 | 33.62 |
| MS - SEM | 1.11 | 1.53 | 2.95 |

TABLE 6

Relative Blood Flow in the Vagina
Normalized by the Blood Flow in the Leg Muscle

|  | Control | Low Dose | High Dose |
| --- | --- | --- | --- |
| VG/MS - mean | 2.07 | 3.02 | 3.02 |
| VG/MS - SEM | 0.11 | 0.29 | 0.18 |

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. Accordingly, the foregoing description should not be read as pertaining only to the precise methods described, but rather should be read consistent with and as support to the following claims which are to have their fullest and fair scope.

I claim:

1. A method for treating female sexual dysfunction or for female sexual enhancement comprising administering to the vagina a composition comprising a prostanoid compound having a vasodilating effect in a pharmaceutically acceptable vehicle, wherein the amount of prostanoid compound administered ranges from about 0.05 mg to about 2 mg.

2. The method according to claim 1, wherein the amount of prostanoid compound administered ranges from about 0.125 mg to about 0.50 mg.

3. The method according to claim 1, wherein the amount of prostanoid compound administered ranges from about 0.125 mg to about 1 mg.

4. The method according to claim 1, wherein the prostanoid compound is lyophilized.

5. The method according to claim 1, wherein the prostanoid compound is encapsulated within liposomes.

6. The method according to claim 5, wherein the liposomes are lyophilized.

7. The method according to claim 1, wherein the pharmaceutically acceptable vehicle is methylcellulose.

8. The method according to claim 1, wherein the composition is administered intravaginally.

9. The method according to claim 1, wherein the composition is administered extravaginally.

10. The method according to claim 1, wherein the prostanoid compound is prostaglandin E-1.

11. The method according to claim 10, wherein the amount of prostanoid compound administered ranges from about 0.125 mg to about 0.50 mg.

12. The method according to claim 10, wherein the amount of prostanoid compound administered ranges from about 0.125 mg to about 1 mg.

13. The method according to claim 10, wherein the prostanoid compound is encapsulated within liposomes.

14. The method according to claim 13, wherein the liposomes are lyophilized.

15. The method according to claim 10, wherein the pharmaceutically acceptable vehicle is methylcellulose.

16. The method according to claim 1, wherein the composition further comprises a surfactant capable of enhancing the bioavailability of the prostanoid compound.

17. A method for treating female sexual dysfunction or for female sexual enhancement comprising administering to the vagina a composition comprising lyophilized liposomal prostaglandin E-1 in methylcellulose, wherein the amount of prostaglandin E1 administered ranges from about 0.125 mg to about 1 mg.

18. A method for enhancing blood flow in the vagina of a patient comprising administering to the vagina a composition comprising a prostanoid compound having a vasodilating effect in a pharmaceutically acceptable vehicle, wherein the amount of prostanoid compound administered ranges from about 0.05 mg to about 2 mg.

19. The method according to claim 18, wherein the amount of prostanoid compound administered ranges from about 0.125 mg to about 0.50 mg.

20. The method according to claim 18, wherein the amount of prostanoid compound administered ranges from about 0.125 mg to about 1 mg.

21. The method according to claim 18, wherein the prostanoid compound is prostaglandin E-1.

* * * * *